United States Patent
Yamada

(10) Patent No.: US 9,486,576 B2
(45) Date of Patent: Nov. 8, 2016

(54) CONTROLLING SYSTEM FOR MEDICAL PUMP

(71) Applicant: Terumo Kabushiki Kaisha, Tokyo (JP)

(72) Inventor: Kazuhiro Yamada, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/663,268

(22) Filed: Mar. 19, 2015

(65) Prior Publication Data

US 2015/0273143 A1  Oct. 1, 2015

(30) Foreign Application Priority Data

Mar. 27, 2014 (JP) ................................. 2014-065789

(51) Int. Cl.
| | |
|---|---|
| *A61M 5/168* | (2006.01) |
| *A61M 5/14* | (2006.01) |
| *G06F 19/00* | (2011.01) |

(52) U.S. Cl.
CPC ........... *A61M 5/168* (2013.01); *A61M 5/1415* (2013.01); *G06F 19/34* (2013.01); *G06F 19/3418* (2013.01); *G06F 19/3468* (2013.01); *A61M 2205/502* (2013.01); *A61M 2205/60* (2013.01); *G06F 19/30* (2013.01); *G06F 19/3406* (2013.01); *G06F 19/3456* (2013.01)

(58) Field of Classification Search
USPC ............................................... 604/75; 705/2
See application file for complete search history.

(56) References Cited

U.S. PATENT DOCUMENTS

| | | | | |
|---|---|---|---|---|
| 2005/0055242 A1* | 3/2005 | Bello | .................. | G06F 19/3468 705/2 |
| 2010/0287006 A1* | 11/2010 | Cannon | .................. | G06F 19/327 705/3 |

FOREIGN PATENT DOCUMENTS

| | | |
|---|---|---|
| JP | 2008-167888 | 7/2008 |
| WO | WO 2013/109517 | 7/2013 |

OTHER PUBLICATIONS

Extended European Search Report for European Patent Application No. 15159214.4, dated Aug. 17, 2015, 7 pages.

* cited by examiner

*Primary Examiner* — Leon-Viet Nguyen
(74) *Attorney, Agent, or Firm* — Sheridan Ross PC

(57) ABSTRACT

Provided is a medical pump monitoring system in which operating states of multiple medical pumps used in hospitals can be intensively monitored through a monitor. The medical pump management system includes a plurality of medical pumps, a transmitting unit that is provided in each of the medical pumps and transmits pump identification information of each of the medical pumps, a receiving unit that is installed in each of the beds and receives the pump identification information transmitted from the transmitting unit, an input/output control unit that causes the bed which has received the pump identification information to be associated with the medical pump, and a display unit that displays the operating state of the medical pump.

20 Claims, 10 Drawing Sheets

FIG. 2

| ICU | | | | |
|---|---|---|---|---|
| BED B1 | BED B2 | BED B3 | BED B4 | |
| P2: 100.00 mL/h | P1: 100.00 mL/h | | | |
| P3: 3.00 mL/h | | | | |
| P4: 3.00 mL/h | | | | |
| BED B5 | | | BED B6 | |

37

CONTROLLING SYSTEM FOR MEDICAL PUMP

CROSS REFERENCE TO RELATED APPLICATIONS

This application claims priority to JP2014-065789, filed Mar. 27, 2014, entitled "Controlling System for Medical Pump", which is incorporated herein by reference in its entirety and for all purposes.

TECHNICAL FIELD

The embodiments herein generally relates to a medical pump management system, and particularly relate to a system for managing a plurality of medical pumps used in hospitals.

BACKGROUND

A medical pump system has been proposed which aims to prevent drug solutions from being erroneously dosed due to misidentification of patients, and in which a patient is associated with a medical pump, such as, a syringe pump and an infusion pump in one-to-one correspondence. The medical pump system is configured to have a communication unit provided in a rack for installing the medical pump and to have external communication means and storage means provided in each medical pump. In such a medical pump system, patient data stored in a first medical pump which has already been installed in the rack is collated with patient data stored in a second medical pump which is newly installed in the rack. Then, installation of the second medical pump is completed when only the items of collated patient data coincide with each other, thereby preventing the misidentification of patients.

SUMMARY

Technical Problem

Incidentally, since multiple medical pumps are used in hospitals adopting the medical pump, it is difficult to promptly and efficiently detect which pump is used in which patient and in which operating state. In the above-described medical pump system, even though misidentification of patients can be prevented by associating a patient with the medical pump, it is difficult to intensively detect the operating state of each medical pump, which is arranged in association with each bed.

Thus, the embodiments aim to provide a medical pump monitoring system in which the operating states of the multiple medical pumps used in hospitals can be intensively monitored through a monitor in a condition close to an actual use condition so as to be able to promptly cope with an abnormal operation of the pump.

Solution to Problem

There is provided a medical pump management system for managing operating states of a plurality of medical pumps in a region where a plurality of beds are arranged. The medical pump management system includes the plurality of medical pumps; a transmitting unit that is provided in each of the medical pumps and transmits pump identification information of each of the medical pumps; a receiving unit that is installed in each of the beds and receives the pump identification information transmitted from the transmitting unit; an input/output control unit that causes the bed, including the installed receiving unit which has received the pump identification information, to be associated with the medical pump provided with the transmitting unit, which has transmitted the pump identification information when any one of the receiving units receives the pump identification information; and a display unit that displays the operating state of the medical pump associated with the bed, in accordance with an instruction from the input/output control unit, in association with the bed.

In the medical pump management system having such a configuration, since the operating states of the plurality of pumps are displayed in association with each bed, the operating states of the multiple medical pumps used in hospitals can be intensively monitored through a monitor in a condition close to an actual use condition.

Advantageous Effects

As a result, operating states of multiple medical pumps used in hospitals can be intensively monitored through a monitor in a condition close to an actual use condition. Therefore, it is possible to promptly cope with an abnormal operation of the medical pump, for example.

BRIEF DESCRIPTION OF DRAWINGS

FIG. 2 is a diagram showing a display image of a display unit in the medical pump management system;

DETAILED DESCRIPTION

Figure 1:
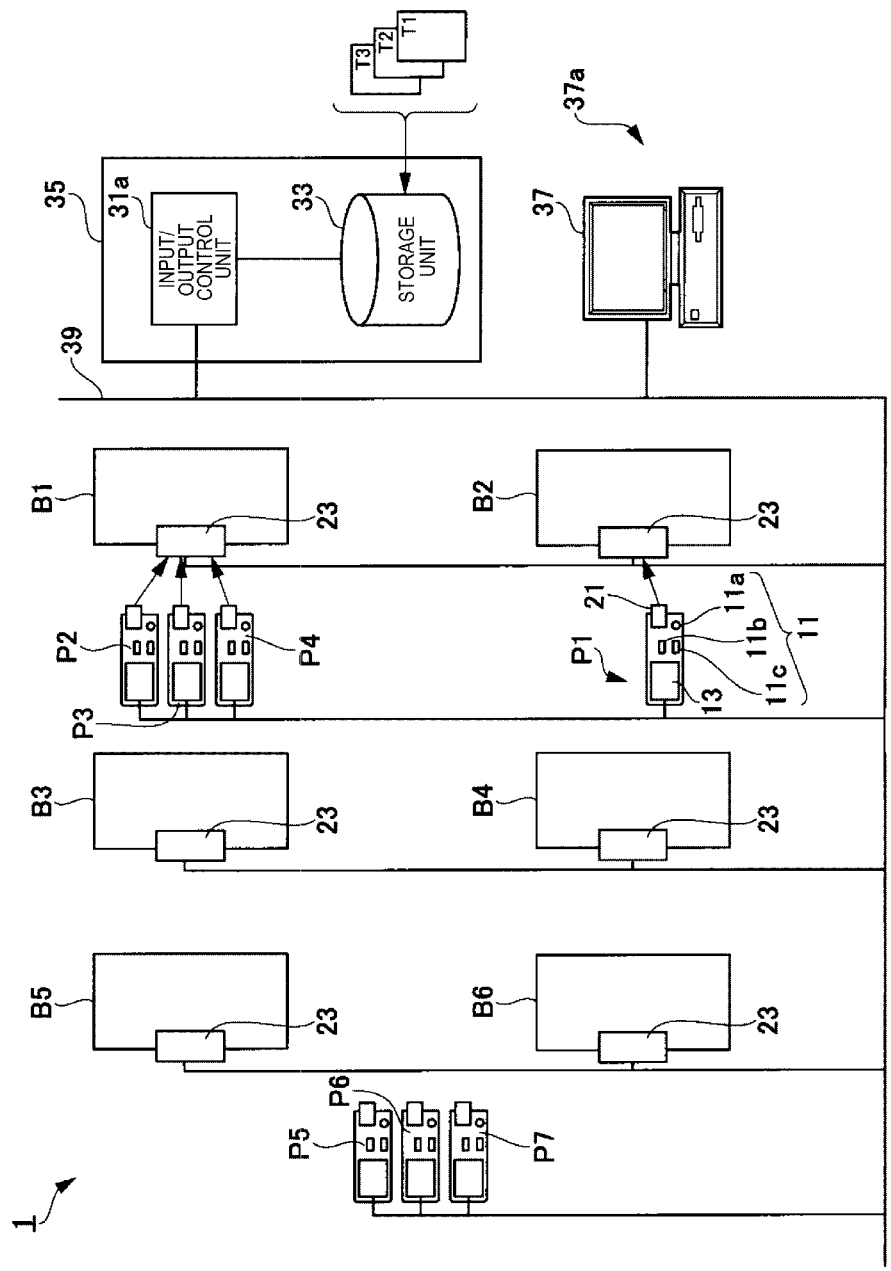
FIG. 1 is a configuration diagram of a medical pump management system.

Hereinafter, embodiments regarding a medical pump management system will be described in detail with reference to the drawings. Note that, in each of the embodiments, the same reference numerals and signs are applied to the same configuration elements, thereby omitting the repeated descriptions.

<<Configuration of Medical Pump Management System>>

FIG. 1 is a configuration diagram of a medical pump management system. The medical pump management system (hereinafter, simply referred to as "the system") 1, shown in FIG. 1, is a system to be applied when intensively managing operating states of a plurality of medical pumps P1, P2, and so forth (hereinafter, representatively referred to as "the pump Pn") within a region where a plurality of beds B1 to B6 (for medical use (hereinafter, representatively referred to as "the bed Bm") are arranged.

Here, the region, having the plurality of beds Bm, is an intensive care unit, a hospital room, or a floor having multiple hospital rooms, for example. In this case, as an example, the region where the six beds B1 to B6 are arranged is referred to as a management region, and descriptions will be given regarding a case of managing the operating states of the plurality of pumps P1, P2, and so forth in the management region.

The system 1 has the plurality of pumps Pn, transmitting units 21 respectively provided in the pumps Pn, and receiving units 23 respectively installed in the beds Bm. The system 1 has a server 35 having an input/output control unit 31a and a storage unit 33, and a display unit 37. For example, the display unit 37 is a display unit of a personal computer 37a. For example, the configuration elements are capable of network communication through a communication network provided in the management region. For example, the communication network is an in-hospital LAN 39. The in-hospital LAN 39 may be a wireless LAN, without being limited thereto. Hereinafter, each of the configuration elements will be described in detail.

<Pump Pn>

The pump Pn is a general medical pump such as a syringe pump and/or an infusion pump. Each pump Pn has a operation unit 11. For example, the operation unit 11 includes a power source operation unit 11a, a start operation unit 11b for starting a pumping operation, and a stop operation unit 11c for stopping a pumping operation. Even though illustration is omitted here, a flow rate/dosage setting operation unit and a display switching operation unit are also included. The pump is operated by a pump operate unit, which is configured to be operated by the operation unit 11.

The pump Pn has a pump display unit 13. For example, the pump display unit 13 is a liquid crystal display panel. The pump display unit 13 may function as a touch panel. In that case, the touch panel is also used as the operation unit. Moreover, the pump Pn may be provided with a warning sound generation unit for generating a warning sound, as necessary.

Each pump Pn described above has external communication means and is connected to the in-hospital LAN 39. The input/output control unit 31a in the server 35 controls an operational state of the operation unit 11, a display on the pump display unit 13, and generation of a warning sound from the warning sound generation unit.

<Transmitting Unit 21>

The transmitting unit 21 is provided in each pump Pn and transmits individual identification information of each pump Pn wirelessly. The transmitting unit 21 is a transmitting unit for short-range wireless communication and performs wireless communication within a range from several centimeters to several meters. For example, the aforementioned transmitting unit 21 is an radio frequency (RFID) tag applied with RFID technology. The individual identification information is stored in the transmitting unit 21, and the transmitting unit 21 transmits the stored individual identification information. Note that, the transmitting unit 21 can be an active tag which spontaneously transmits the individual identification information. The transmitting unit 21 may be previously built in each pump Pn.

Note that, the individual identification information transmitted from the transmitting unit 21 becomes pump identification information in which the transmitting unit 21 is associated with the pump Pn on a one-to-one basis. Therefore, the individual identification information transmitted from the transmitting unit 21 may coincide with the individual identification information which the pump Pn originally has, and does not have to coincide therewith.

The aforementioned individual identification information transmitted from the transmitting unit 21, that is, the pump identification information is previously stored in a pump identification information table T1 of the storage unit 33 described below, as the transmitting unit-pump association information.

<Receiving Unit 23>

The receiving unit 23 receives the pump identification information transmitted from the transmitting unit 21. As for each receiving unit 23, if the transmitting unit 21 is the RFID tag, the receiving unit 23 is an RFID reader, which receives the pump identification information transmitted from the transmitting unit 21 by wireless communication within a range from several centimeters to several meters. Each receiving unit 23 has the individual identification information and is installed in each bed Bm in a state of being individually associated with each bed Bm provided in the management region on a one-to-one basis. Therefore, the individual identification information included in the receiving unit 23 is bed identification information which is associated with the bed Bm on a one-to-one basis, thereby being stored in a bed identification information table T2 of the storage unit 33 described below, as receiving unit-bed association information.

Each receiving unit 23 described above is connected to the in-hospital LAN 39 and is configured to transmit the bed identification information included in the receiving unit 23 itself to the input/output control unit 31a, together with the received pump identification information when the pump identification information transmitted from the transmitting unit 21 is received.

Note that, for example, the above-described receiving unit-bed association information is stored in the bed identification information table T2 of the storage unit 33 through an input operation from the personal computer 37a.

<Input/output Control Unit 31a (Server 35)>

The input/output control unit 31a controls the system 1 and configures the server 35 together with the storage unit 33. The input/output control unit 31a causes the pump Pn to be associated with the bed Bm based on the pump identification information received in the receiving unit 23 which is installed in each bed Bm, the bed identification information of the receiving unit 23, which has received the pump identification information, and information stored in the storage unit 33.

The bed Bm is associated with the pump Pn by the input/output control unit 31a as follows. Firstly, if the pump identification information is received in any one of a plurality of the receiving units 23, the received pump identification information, and the bed identification information of the receiving unit 23, which has received the pump identification information, are transmitted to the input/output control unit 31a via the in-hospital LAN 39. The input/output control unit 31a specifies the pump Pn based on the received pump identification information, and the pump identification information table T1 of the storage unit 33. Moreover, the input/output control unit 31a specifies the bed Bm based on the received bed identification information, and the bed identification information table T2 of the storage unit 33. Then, the specified pump Pn is associated with the specified bed Bm.

In the illustrated example, as the pumps P2, P3, and P4 are arranged close to the bed B1, the receiving unit 23 installed in the bed B1 receives the pump identification information transmitted from each transmitting unit 21 provided in the pumps P2, P3, and P4. The received pump identification information is transmitted to the input/output control unit 31a via the in-hospital LAN 39, together with the bed identification information of the receiving unit 23, which has received the pump identification information.

Accordingly, the input/output control unit 31a specifies the pumps P2, P3, and P4, and also specifies the bed B1 based on each piece of the received pump identification information and bed identification information, as well as the pump identification information table T1 and bed identification information table T2 of the storage unit 33, thereby causing the pumps and the bed to be associated with each other. Similarly, the bed B2 is associated with the pump P1.

Meanwhile, the pump Pn which is arranged away from any one of the beds Bm exceeding a prejudged interval is associated with none of the beds Bm. Here, a prejudged interval denotes a distance in which the transmitting unit 21 provided in the pump Pn and the receiving unit 23 installed in the bed Bm can communicate with each other.

The input/output control unit 31a causes association information of the beds Bm and the pumps Pn associated with each other as described above to be stored in a bed-pump associated table T3 of the storage unit 33.

The input/output control unit 31a causes the display unit 37 to display the association information of the bed Bm and the pump Pn as well as the operating state of the pump Pn associated with each bed Bm.

Moreover, the input/output control unit 31a controls starting of a pumping operation of each pump Pn associated with the bed Bm, and a non-associated pump Pn which is associated with none of the beds Bm, via the in-hospital LAN 39. Specifically in the illustrated example, only the pumps P1 to P4 which are associated with the beds B1 and B2 are allowed to be operated by the start operation unit 11b provided in the pumps P1 to P4. Meanwhile, pumps P5 to P7 associated with none of the beds B1 to B6 are inhibited from being operated by the start operation unit 11b.

<Storage Unit 33 (Server 35)>

The storage unit 33 configures the server 35 together with the input/output control unit 31a and stores association related information and other pieces of information via the input/output control unit 31a. The association related information stored in the storage unit 33 is the pump identification information table T1, the bed identification information table T2, the bed-pump associated table T3, or the like described above.

<Display Unit 37 (Personal Computer 37a)>

For example, the display unit 37 is a display unit of the personal computer 37a and displays the operating state of the pump Pn associated with each bed Bm in accordance with an instruction from the input/output control unit 31a. FIG. 2 shows an example of a display image in the display unit 37. As shown in FIG. 2, the display unit 37 displays the operating states of the pumps P1, P2, and so forth individually associated with the beds B1 to B6. In this case, for example, display areas for each of the beds B1 to B6 are set. In each of the set areas, identification information for identifying the pumps P1, P2, and so forth individually associated with the beds B1 to B6 is displayed (here, displayed as P1, P2, and so forth, for example), and the operating states of each of the pumps P1, P2, and so forth (a flow rate per hour, for example) are displayed in succession.

In the illustrated example, three pumps P2, P3, and P4 are associated with the bed B1, and one pump P1 is associated with the bed B2. The operating state of each pump Pn is displayed in each display portion.

For example, the operating states of the pumps P1, P2, and so forth may be differentiated in stages of a normal operating display, a preliminary warning display, a warning display, or the like, and color of a backlight may be allocated for each stage, thereby displaying the operating states in the display unit 37 in accordance with an instruction from the input/output control unit 31a. For example, if the operating states of the pumps P2 and P3 associated with the bed B1 are in normal states, the backlight is blue for the display. If the operating state of the pump P4 associated with the bed B1 is in an abnormal state, the backlight is red for the display. If the operating state of the pump P1 associated with the bed B2 is in the preliminary warning state instead of the normal operating state, the backlight is yellow for the display.

The above-described display unit 37 may be installed in the management region where the plurality of beds Bm are arranged, may be installed in a nurse station outside the management region, or may be installed in both thereof.

Note that, in the illustrated example, the identification information for identifying the pump Pn is configured to be displayed together with the operating state of the pump Pn. However, it is not necessary to display all thereof on one display screen. For example, only the operating state of the pump Pn may be configured to be displayed in each display portion on one display screen, and thereby clicking each display portion of the operating state displays identification information of a specific pump Pn or further detailed pump information (a drug solution to be dosed, a dosage, or the like) of the corresponding operating state.

<Method of Managing Medical Pump>

Figure 3:
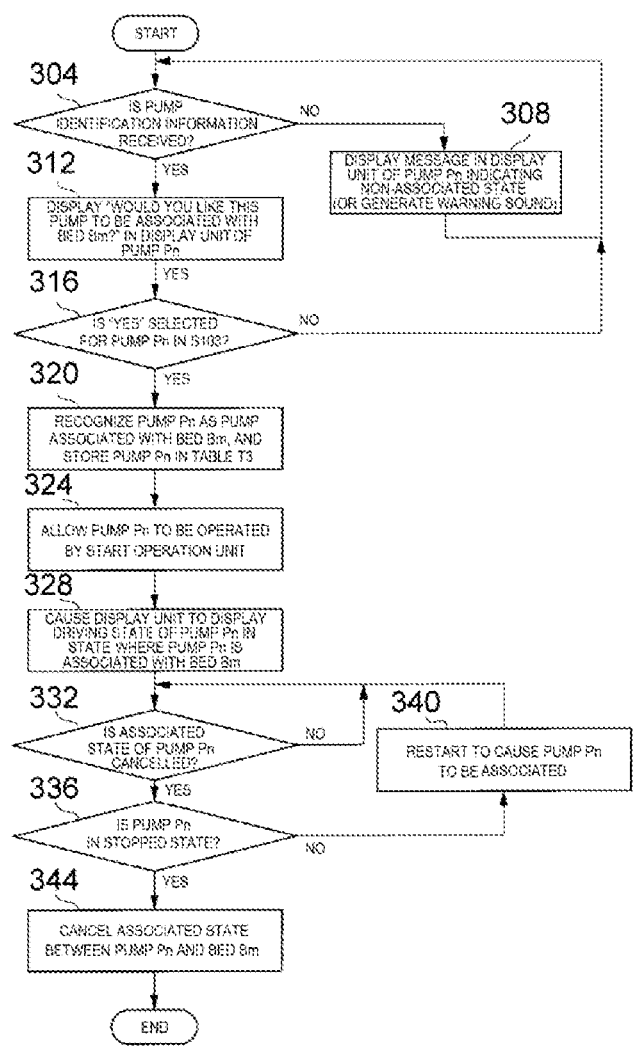
FIG. 3 is a flowchart illustrating an embodiment of a method of managing pumps in the medical pump management system.

Subsequently, in the system 1 having the above-described configuration, descriptions will be given regarding procedures of a method of managing a medical pump executed by the input/output control unit 31a. FIG. 3 is a flowchart showing the management method. Hereinafter, with reference to preceding FIGS. 1 and 2, the method of managing a medical pump will be described in accordance with the flowchart in FIG. 3. Here, the description will be given regarding a case where a specific pump Pn is operated for a specific bed Bm in the management region.

[Step 304]

Firstly, in Step 304 after starting the processing, it is judged whether the pump identification information is received in using the receiving unit 23 installed in any one of the beds Bm in the management region. If a target pump Pn is away from all the beds Bm exceeding a prejudged interval, the pump identification information is not received. Thus, it is judged to be "No" and the procedure proceeds to Step 308. Meanwhile, if the pump Pn approaches any one of the beds Bm within a prejudged interval, the pump identification information of the pump Pn is received in the receiving unit 23 of any one of the beds Bm. Thus, it is judged to be "Yes" and the procedure proceeds to Step 312.

[Step 308]

If it is judged to be "No" in Step 304 and the procedure proceeds to Step 308, the input/output control unit 31a displays a message indicating a non-associated state in the pump display unit 13 of the pump Pn, causes the pump Pn to generate a warning sound, or performs both thereof in Step 308. Then, Steps 309 and 308 are repeated until it is judged to be "Yes" in Step 304.

[Step S103]

If it is judged to be "Yes" in Step 304 and the procedure proceeds to Step 312, the pump identification information of the pump Pn is received in the receiving unit 23 of any one of the beds Bm. Therefore, the input/output control unit 31a causes the pump display unit 13 in the pump Pn to display "Would you like this pump to be associated with the bed Bm?"

In this case, the input/output control unit 31a specifies the pump Pn based on the transmitted pump identification information and the pump identification information table T1 of the storage unit 33. The bed Bm is also specified based on the bed identification information transmitted together with the pump identification information, and the bed identification information table T2 of the storage unit 33. Then, the pump display unit 13 in the specified actual pump Pn is instructed so as to display "Would you like this pump to be associated with the bed Bm?" as a determination display to judge whether or not the pump is associated with the specified bed Bm.

If the bed Bm subjected to such a determination display coincides with the target bed Bm, "Yes" is selected in the operation unit 11 on the actual pump Pn.

[Step 316]

In Step 316, it is judged whether "yes" is selected on the actual pump Pn against the question "Would you like this pump to be associated with the bed Bm?" of the pump display unit in preceding Step 312. If it is judged that "Yes" is selected, the procedure proceeds to Step 320. If it is not judged that "Yes" is selected, the procedure returns back to Step 304, and Steps 304 to 316 are repeated until it is judged to be "Yes" in Step 316.

In the meantime, the pump Pn is repeatedly moved until the pump identification information of the pump Pn is received in the receiving unit 23 of the target bed Bm. Accordingly, the pump Pn is reliably associated with the target bed Bm.

[Step 320]

In Step 320, if it is judged to be "Yes" in preceding Step 316, the input/output control unit 31a recognizes the pump Pn as a pump associated with the bed Bm, thereby storing the pump Pn in the bed-pump associated table T3 of the storage unit 33.

[Step 324]

In Step 324, the input/output control unit 31a allows the pump Pn to be operated by the start operation unit 11b. According to such controlling of the pump Pn performed by the input/output control unit 31a, a pumping operation can start in the pump Pn, thereby operating the pump Pn according to prejudged procedures.

[Step 328]

In Step 328, the input/output control unit 31a causes the display unit 37 of the personal computer 37a to display the operating state of the pump Pn in a state where the pump Pn is associated with the bed Bm. A display in the display unit 37 is as previously described with reference to FIG. 2.

[Step 332]

In Step 332, the input/output control unit 31a judges whether or not the associated state of the pump Pn is cancelled with respect to the bed Bm. Step 332 is repeated until it is judged to be cancelled, "Yes". If it is judged to be cancelled, "Yes", the procedure proceeds to the following Step 336.

In other words, if it is intended to complete operating of the pump Pn, the actual pump Pn is operated by the operation unit 11 in the actual pump Pn so as to cancel the associated state with respect to the bed Bm. The input/output control unit 31a detects the cancellation of the associated state with respect to the bed Bm in the actual pump Pn.

[Step 336]

In Step 336, if it is judged that the associated state with respect to the bed Bm in the actual pump Pn is cancelled in preceding Step 332, it is judged whether or not the pump Pn is in a stopped state. If it is judged not to be in the stopped state, "No", the procedure proceeds to Step 340. Meanwhile, if it is judged to be in the stopped state, "Yes", the procedure proceeds to Step 344.

[Step 340]

In Step 340, since it is judged that the pump Pn is not in the stopped state, "No" in preceding Step 336, the input/output control unit 31a restarts to cause the pump Pn to be associated with the bed Bm in the actual pump Pn. Thereafter, Steps 332 and 336 are repeated, and the associated state between the pump Pn and the bed Bm cannot be cancelled as long as the pump Pn is not in the stopped state. Accordingly, even though the pump Pn is in the operating state, the associated state in the pump Pn is prevented from being cancelled, and actual dosing history of a drug solution using the pump Pn and a dosing record to be stored in the server 35 are prevented from being inconsistent.

[Step 344]

In Step 344, if the pump Pn is judged to be in the stopped state, "Yes" in preceding Step 336, the input/output control unit 31a cancels the associated state between the pump Pn and the bed Bm. Accordingly, the display of the pump Pn is deleted from the display unit 37. The association information of the pump Pn and the bed Bm is deleted from the bed-pump associated table T3 of the storage unit 33. Accordingly, it is possible to move the pump Pn from the side of the bed Bm.

<Advantageous Effect>

As described above, the medical pump management system 1 is configured to display the operating state of each pump Pn by causing the plurality of beds Bm to be individually associated with the pumps Pn. Therefore, the operating states of the multiple pumps Pn used in hospitals can be intensively monitored as information for each bed Bm through a monitor in a condition close to an actual use condition. Accordingly, for example, if an abnormal operation of the pump Pn is detected, it is possible to promptly grasp the bed Bm using the pump Pn, and the pump Pn. Thus, it is possible to promptly cope with the abnormal operation of the pump Pn.

Moreover, as shown in Step 324, the above-described medical pump management system 1 is configured to allow only the pump Pn associated with the specified bed Bm to be operated by the start operation unit 11b in the pump Pn. Therefore, even though the plurality of pumps are arranged at a bedside, the target pump Pn associated with the bed Bm can be reliably operated. Thus, it is possible to prevent the pump Pn to be operated from being erroneously selected.

Moreover, as the procedures of Steps 332 to 340 are performed, the associated state is configured to be cancelled with respect to the specified bed Bm only if the operating of the specified medical pump Pn is in the stopped state. Therefore, even though the pump Pn is in the operating state, the associated state in the pump Pn can be prevented from being cancelled, and the pump Pn can be prevented from being erroneously operated, as well. Accordingly, actual dosing history of a drug solution using the pump Pn and a dosing record to be stored in the storage unit 33 of the server 35 can be also prevented from being inconsistent.

<<Additional or Alternative Configuration of Medical Pump Management System>>

Figure 4:
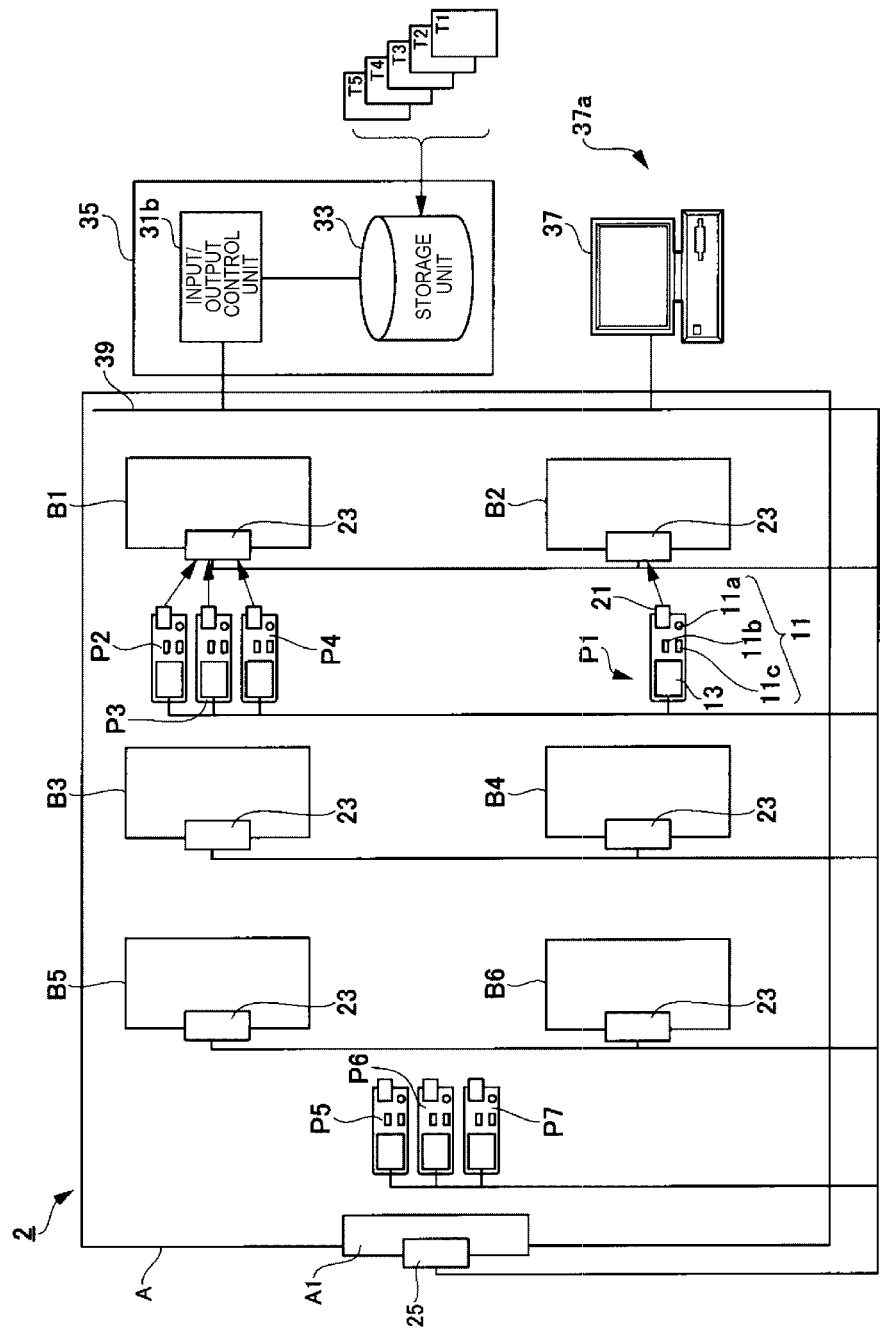
FIG. 4 is a configuration diagram of a medical pump management system.

FIG. 4 is another configuration diagram showing a medical pump management system. The medical pump management system 2 (hereinafter, simply referred to as "the system 2") shown in FIG. 4 is different from the system 1 in that the region where the beds Bm are arranged is a management region A, and an entrance receiving unit 25 is installed at an entrance A1 of the management region A. An input/output control unit 31b performs pump management utilizing received information in the entrance receiving unit 25. Since the configuration other than the management procedures executed by the entrance receiving unit 25 and the input/output control unit 31b described above is the same, the same reference numerals and signs are applied to the configuration elements similar to those of the embodiments above. Overlapping descriptions will be omitted.

Note that, the management region A set in this case is an intensive care unit, a hospital room, or a floor having multiple hospital rooms, for example. In this case, as an example, the region where the six beds B1 to B6 (representatively, the bed Bm) are arranged is referred to as a management region, and descriptions will be given regarding a case of managing the operating states of the pumps P1, P2, and so forth (representatively, the pump Pn) in the management region.

<Entrance Receiving Unit 25>

The entrance receiving unit 25 receives the pump identification information transmitted from the transmitting unit 21. The entrance receiving unit 25 may be the RFID reader similar to the receiving unit 23 provided in each bed Bm. The entrance receiving unit 25 is connected to the in-hospital LAN 39 and is installed at a position where the pump identification information transmitted from the transmitting unit 21 can be received in the entrance A1 of the management region A or in the vicinity of the entrance A1. Note that, if a plurality of the management regions are present, the entrance receiving unit is associated with one management region on a one-to-one basis. Such association is performed through an input operation from the personal computer 37a, for example, and the association information is stored in a region information table T4 as entrance receiving unit-management region association information of the storage unit 33.

<Input/output Control Unit 31b (Server 35)>

The input/output control unit 31b controls the system 2 and configures the server 35 together with the storage unit 33. Similarly to the first embodiment, the input/output control unit 31b causes the pump Pn to be associated with the bed Bm based on the pump identification information received in the receiving unit 23 which is installed in each bed Bm, the bed identification information of the receiving unit 23 which has received the pump identification information, and information stored in the storage unit 33.

In a case where a certain pump Pn is carried in the management region A, if the pump identification information transmitted from the transmitting unit 21 of the pump Pn is received in the entrance receiving unit 25 as the pump Pn passes the entrance A1 of the management region A, the input/output control unit 31b recognizes the received state. Then, the pump Pn is associated with the management region A based on the region information table T4 and the pump identification information table T1 stored in the storage unit 33. Then, the pump identification information of the pump Pn associated with the management region A is stored in a pump table T5 in the management region of the storage unit 33.

Similarly to the first embodiment, the input/output control unit 31b causes the display unit 37 to display the association information of the bed Bm and the pump Pn as well as the operating state of the pump Pn associated with each bed Bm. Moreover, the input/output control unit 31b also causes the display unit 37 to display the pump Pn stored in the pump table T5 of the storage unit 33 as a non-associated pump Pn in the management region A.

Figure 5:
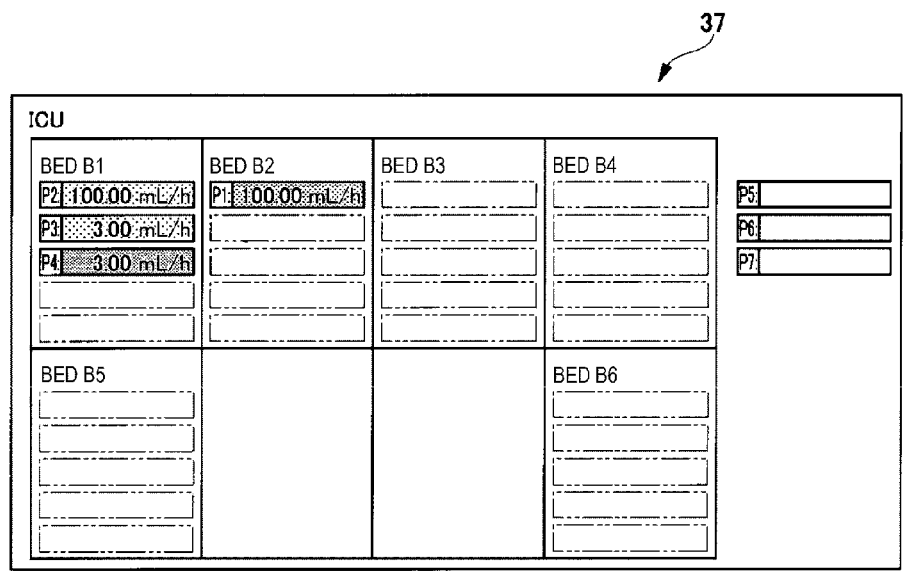
FIG. 5 is a diagram showing a screen of the display unit in the medical pump management system.

In the example shown in FIG. 5, the input/output control unit 31b causes the display unit 37 to display the operating states of the pumps P2, P3, and P4 in association with the bed B1. Moreover, the operating state of the pump P1 is displayed in association with the bed B2. As the non-associated pump Pn which is carried in the management region A but is associated with none of the beds B1 to B6, the pumps P5 to P7 are displayed outside the display areas for the beds B1 to B6.

The input/output control unit 31b inhibits each pump Pn which is carried in the management region A but is associated with none of the beds Bm, from being operated by the start operation unit 11b.

<Method of Managing Medical Pump>

Figure 6:
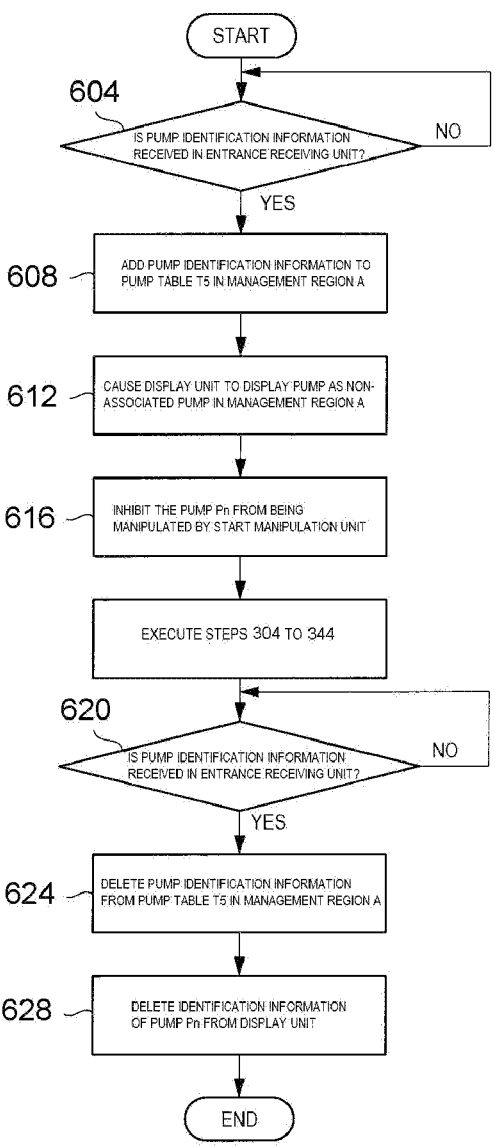
FIG. 6 is a flowchart illustrating an embodiment of a method of managing pumps in the medical pump management system.

Subsequently, in the system 2 having the above-described configuration, descriptions will be given regarding procedures of a method of managing a medical pump executed by the input/output control unit 31b. FIG. 6 is a flowchart showing the management method. Hereinafter, with reference to preceding FIGS. 4 and 5, the method of managing a medical pump will be described in accordance with the flowchart in FIG. 6.

[Step 604]

Firstly, in Step 604 after starting the processing, it is judged whether or not the pump identification information is received in the entrance receiving unit 25 of the management region A. Here, if the pump Pn is carried in the management region A, since the pump identification information of the pump Pn is received in the entrance receiving unit 25, it is judged to be "Yes", and the procedure proceeds to Step 608. In other cases, it is judged to be "No", thereby repeating Step 604 so as to detect the pump Pn carried in the management region A.

[Step 608]

In Step 608, the input/output control unit 31b stores the received pump identification information in the pump table T5 in the management region A of the storage unit 33.

[Step 612]

In Step 612, the input/output control unit 31b causes the display unit 37 to display the pump Pn of which the pump identification information is stored in the pump table T5 as the non-associated pump Pn in the management region A. In the example shown in FIG. 5, the input/output control unit 31b causes the display unit 37 to display the pumps P5 to P7 as the non-associated pump Pn outside the display areas for the beds B1 to B6.

[Step 616]

In Step 616, the input/output control unit 31b inhibits the pump Pn stored in the pump table T5 from being operated by the start operation unit 11b. Accordingly, it is possible to prevent the non-associated pump Pn which is associated with none of the beds Bm from being erroneously operated, out of the multiple pumps Pn arranged in the management region A.

[Steps 304 to 344]

After the above procedure, Steps 304 to 344 (refer to FIG. 3) described above are executed so as to operate the pump Pn associated with the bed Bm. After the operating thereof is completed, the pump Pn of which the associated state is cancelled with respect to the bed Bm is deleted from the display areas of the beds Bm in the display unit 37 and is deleted from the bed-pump associated table T3 in the storage unit 33. Note that, in Step 344, the pump Pn of which the associated state is cancelled with respect to the bed Bm is displayed in the display unit 37 as the non-associated pump Pn outside the display areas of the beds Bm.

[Step 620]

Thereafter, in Step 620, it is judged whether or not the pump Pn of which the associated state is cancelled with respect to the bed Bm, that is, the pump identification information of the non-associated pump Pn is received in the entrance receiving unit 25. If the pump Pn does not pass the entrance A1, the pump identification information is not received in the entrance receiving unit 25. Thus, it is judged to be "No" and Step 620 is repeated. Meanwhile, if the pump Pn passes the entrance A and is carried out from the management region A, the pump identification information is received in the entrance receiving unit 25. Thus, it is judged to be "Yes" and the procedure proceeds to Step 624.

[Step 624]

In Step 624, the pump identification information of the pump Pn carried out from the management region A is deleted from the pump table T5 in the management region A of the storage unit 33.

[Step 628]

In Step 628, the display of the pump Pn of which the pump identification information is deleted from the pump table T5 is deleted from the display unit 37.

<Advantageous Effects>

As described above, according to the medical pump management system 2, in Step 616, the pump Pn which is carried in the management region A but is associated with none of the beds Bm is inhibited from being operated by the start operation unit 11b. Accordingly, even though the plurality of pumps are arranged at a bedside, only the target pump Pn associated with the target bed Bm can be reliably operated. Thus, it is possible to further reliably prevent the pump Pn to be operated from being erroneously selected.

MODIFICATION EXAMPLE 1

Figure 7:
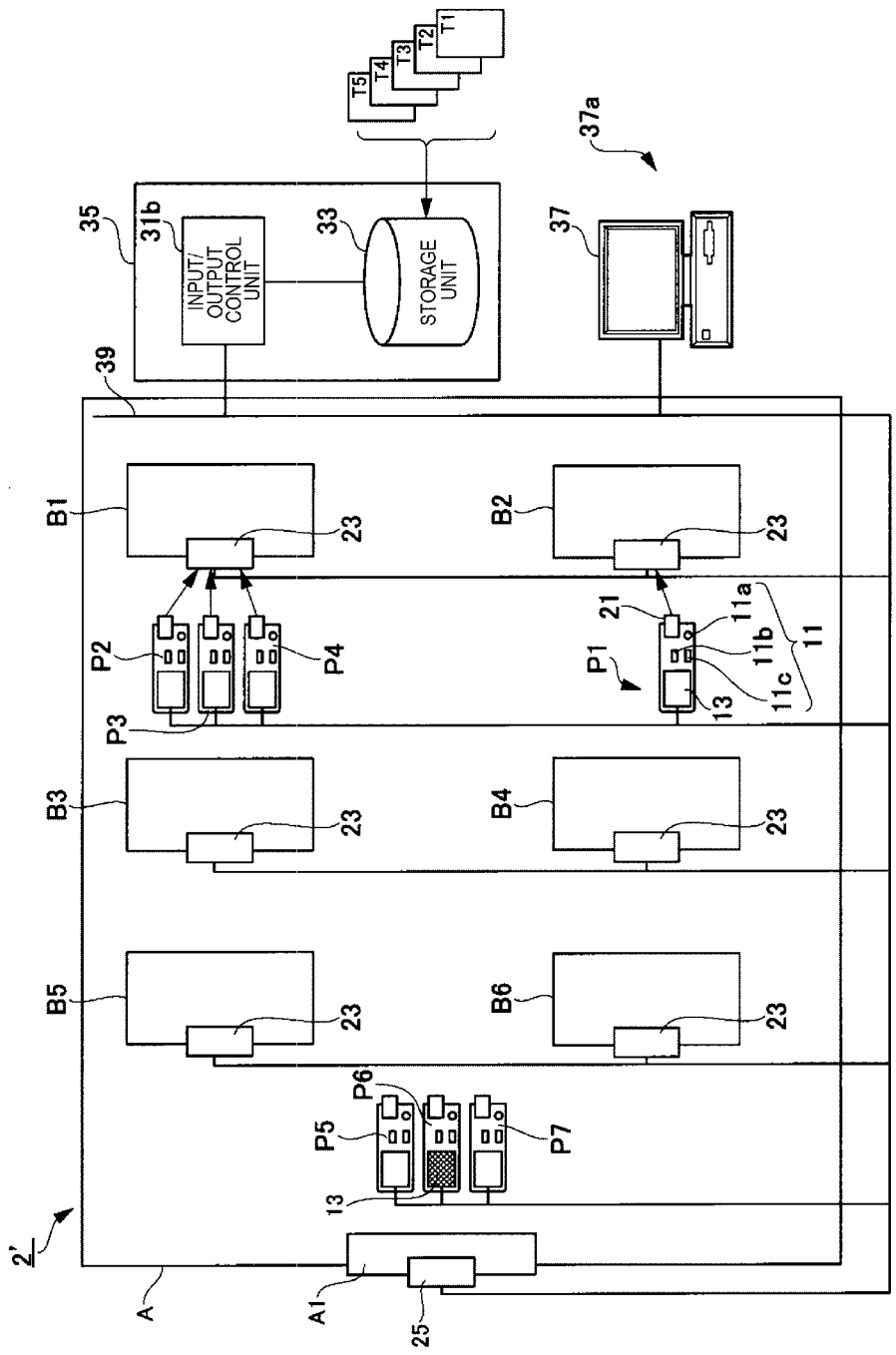
FIG. 7 is a configuration diagram showing Modification Example 1.
Figure 8:
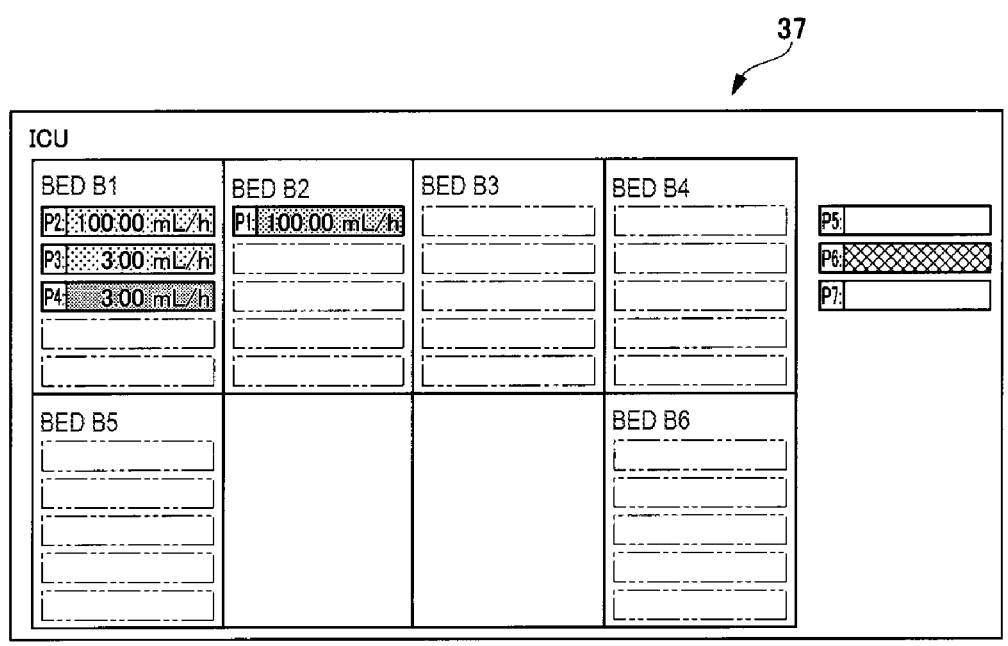
FIG. 8 is a diagram showing a screen of the display unit in Modification Example 1.

FIG. 7 is a first configuration diagram showing Modification Example 1. FIG. 8 is a second diagram showing a screen of the display unit in Modification Example 1. If the identification information of the pump Pn displayed as the non-associated pump in the display unit 37 is selected and clicked, a medical pump management system 2' of Modification Example 1 shown in the diagrams is configured to display the selection information in the pump display unit 13 of the corresponding actual pump Pn. Such a display operation of the pump display unit 13 is performed by the input/output control unit 31b.

In the illustrated example, the display unit 37 displays the identification information of the pumps P5 to P7 (here, for example, P5, P6, and P7) as the non-associated pumps. In this case, the display portion for the identification information of the pump P6 is selected and clicked, thereby displaying the selection information in the pump display unit 13 of the actual pump P6 indicating that selection is made. The selection information displayed in the pump display unit 13 may be a message such as "Selection has been made" or a portion of the pump display unit 13 may be displayed in a reversed color.

Note that, the selection information is not limited to being displayed in the pump display unit 13 of the pump Pn. For example, if the pump Pn includes the warning sound generation unit, the selection information may generate a warning sound from the warning sound generation unit instead of displaying in the pump display unit 13.

Accordingly, if the plurality of pumps Pn are arranged at a bedside, the target pump Pn can be promptly found out from the non-associated pumps Pn which are associated with none of the beds Bm.

MODIFICATION EXAMPLE 2

Figure 9:
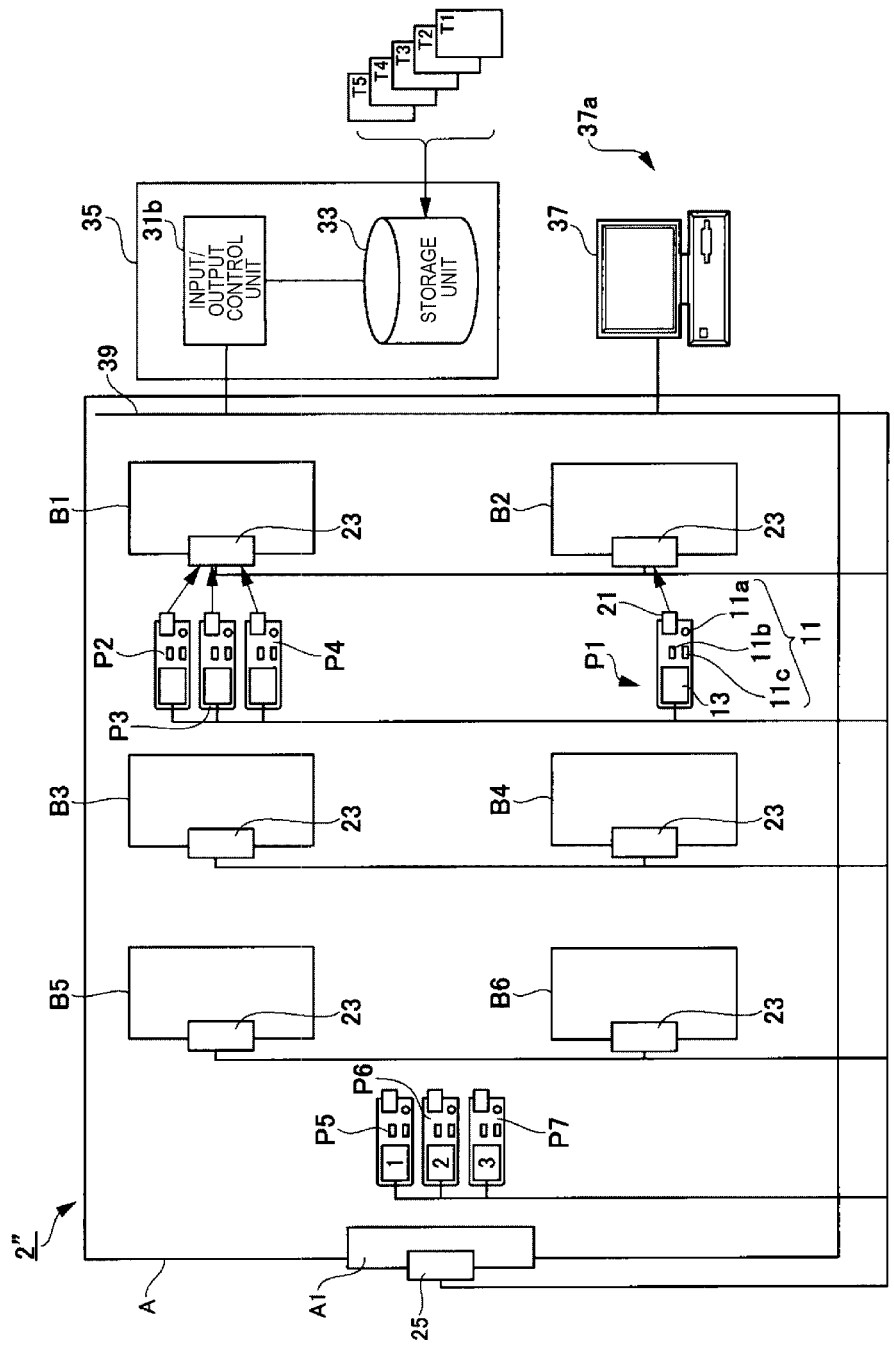
FIG. 9 is a configuration diagram showing Modification Example 2.
Figure 10:
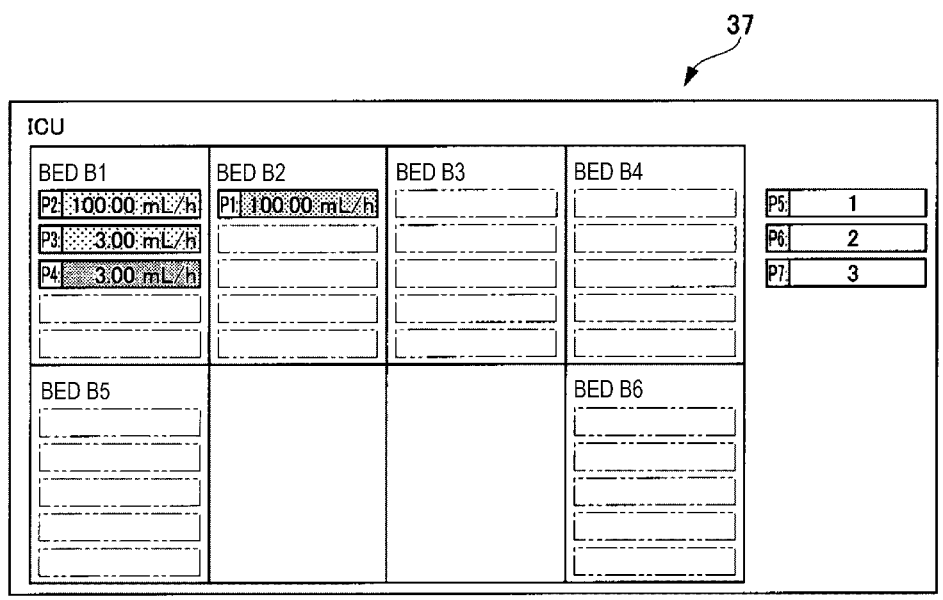
FIG. 10 is a diagram showing a screen of the display unit in Modification Example 2.

FIG. 9 is a first configuration diagram showing Modification Example 2. FIG. 10 is a second diagram showing a screen of the display unit in Modification Example 2. A medical pump management system 2" of Modification Example 2 shown in the diagrams is configured to automatically apply a number to the pump Pn which is recognized as the non-associated pumps, and to display the applied number in the display portion of the non-associated pump in the display unit 37. Similarly, the automatically applied number is displayed in the pump display unit 13 of the actual pump Pn as well. Such displaying is performed by the input/output control unit 31b.

In the illustrated example, the display unit 37 displays the identification information of the pumps P5 to P7 (here, for example, P5, P6, and P7) as the non-associated pump. In this case, numbers 1 to 3 are automatically applied and displayed in the display portion of each of the pumps P5 to P7. The automatically applied numbers 1 to 3 are displayed in the pump display unit 13 of the actual pumps P5 to P7 as well.

Accordingly, if the plurality of pumps Pn are arranged at a bedside, the target pump Pn can be promptly found out from the non-associated pumps Pn which are associated with none of the beds Bm.

Note that, the embodiments are not limited to those embodiments and the modification examples described above and illustrated in the drawings. Thus, various changes and modifications can be made without departing from the scope of the Claims.

REFERENCE SIGNS LIST

1, 2, 2', 2" ... medical pump management system,
11b ... start operation unit (medical pump),
21 ... transmitting unit,
23 ... receiving unit,
25 ... entrance receiving unit,
31a, 31b ... input/output control unit,
37 ... display unit,
A ... management region,
A1 ... entrance,
Bm, B1 to B6 ... bed, and
Pn, P1, P2, and so forth ... pump (medical pump)

What is claimed is:

1. A medical pump management system for managing operating states of a plurality of medical pumps in a region where a plurality of beds are arranged, the system comprising:
   a medical pump, wherein the medical pump comprise:
      a transmitting unit that is provided in the medical pump and transmits pump identification information of the medical pumps;
      a start operation unit to allow the medical pump to start a pumping operation;
   a receiving unit that is in wireless communication with the transmitting unit and installed in a bed, wherein the receiving unit receives the pump identification information from the transmitting unit when the transmitting unit of the medical pump is within physical proximity of the receiving unit;

an input/output control unit in communication with the receiving unit of the bed, wherein the input/output unit automatically associates the bed, including the receiving unit, which has received the pump identification information, with the medical pump, which is provided with the transmitting unit that has transmitted the pump identification information, when the receiving unit receives the pump identification information, and wherein the input/output control unit allows the pump to be operated by the start operation unit if the input/output control unit recognizes the medical pump is associated with the bed within a predetermined interval; and a display unit in communication with the input/output control unit, wherein the display unit displays the operation state of the medical pump installed in the bed in accordance with an instruction from the input/output control unit in association with the bed.

2. The medical pump management system according to claim 1, wherein the region where the plurality of beds, respectively including the installed receiving unit, are arranged is a management region, and wherein the medical pump management system further comprises:

an entrance receiving unit is installed at an entrance of the management region, wherein the entrance receiving unit receives the pump identification information; and wherein the input/output control unit causes a medical pump, associated with no bed but which the pump identification information has been received in the entrance receiving unit, to be displayed in the display unit as a non-associated pump.

3. The medical pump management system according to claim 1, wherein the input/output control unit cancels the association of the medical pump with the bed when the medical pump is in a stopped state of operating.

4. The medical pump management system according to claim 3, wherein the region where the plurality of beds, respectively including the installed receiving units, are arranged is a management region, and wherein the medical pump management system further comprises:

an entrance receiving unit, for receiving the pump identification information, is installed at an entrance of the management region; and wherein the input/output control unit causes a medical pump, associated with no bed but which the pump identification information has been received in the entrance receiving unit, to be displayed in the display unit as a non-associated pump.

5. The medical pump management system according to claim 4, wherein, when the input/output control unit cancels the association of the medical pump with the bed, but when the medical pump remains in the management region, the input/output control unit causes the medical pump to be displayed in the display unit as a non-associated pump.

6. The medical pump management system according to claim 1, wherein the input/output control unit allows only the medical pump associated with any one of the beds to be operated by the start operation unit.

7. The medical pump management system according to claim 6, wherein the region where the plurality of beds, respectively including the installed receiving units, are arranged is a management region, and wherein the medical pump management system further comprises:

an entrance receiving unit, for receiving the pump identification information, is installed at an entrance of the management region; and wherein the input/output control unit causes a medical pump, associated with no bed but which the pump identification information has been received in the entrance receiving unit, to be displayed in the display unit as a non-associated pump.

8. The medical pump management system according to claim 7, wherein, the input/output control unit prevents the non-associated pump from executing the start operation.

9. The medical pump management system according to claim 7, wherein the input/output control unit cancels an associated state of the medical pump with respect to the bed only when the medical pump is judged to be in a stopped state of operating.

10. The medical pump management system according to claim 9, wherein, when the input/output control unit cancels the association of the medical pump with the bed, but when the medical pump remains in the management region, the input/output control unit causes the medical pump to be displayed in the display unit as a non-associated pump.

11. The medical pump management system according to claim 10, wherein, the input/output control unit prevents the medical pump, which has the associated state cancelled, from executing a next start operation.

12. A method for managing operating states of a plurality of medical pumps in a region where a plurality of beds are arranged, the method comprising:

transmitting pump identification information for a medical pump from a transmitting unit, provided in a medical pump, to a receiving unit that is installed in the bed, wherein the medical pump is in physical proximity to the bed, wherein the medical pump comprises a start operation unit to allow the medical pump to start a pumping operation;

the receiving unit associated with the bed receiving the pump identification information transmitted from the transmitting unit, when the transmitting unit of the medical pump is within physical proximity of the receiving unit;

an input/output control unit associating the bed, including the installed receiving unit which has received the pump identification information, with the medical pump provided with the transmitting unit;

and the input/output control unit allowing the medical pump to be operated by the start operation unit if the input/output control unit recognizes the pump as a pump associated with the bed within a prejudged interval; and a display unit displaying the operating state of the medical pump associated with the bed in accordance with an instruction from the input/output control unit in association with the bed.

13. The method according to claim 12, wherein the region where the plurality of beds, respectively including the installed receiving units, are arranged is a management region, and wherein the method further comprises:

providing an entrance receiving unit at an entrance of the management region; and the entrance receiving unit receiving the pump identification information when a second medical pump enters the management region; and the input/output control unit causing the second medical pump, not associated with a bed but which the pump identification information has been received by the entrance receiving unit, to be displayed in the display unit as a non-associated pump.

14. The method according to claim 13, further comprising:

the input/output control unit canceling the association, of the medical pump, with respect to the bed only when the medical pump is judged to be in a stopped state of operating.

15. The method according to claim 14, further comprising:
   the input/output control unit causing the medical pump, having a cancelled association and still within the management region, to be displayed in the display unit as a second non-associated pump.

16. The method according to claim 13, further comprising:
   the input/output control unit allowing the medical pump associated with the bed to be operated by a start operation unit; and
   the start operation unit starting a pumping operation on the medical pump, if the input/output control unit has allowed the operation.

17. A non-transitory computer readable medium having instructions stored thereon for performing a method for managing operating states of a plurality of medical pumps in a region where a plurality of beds are arranged, the method comprising:
   receiving pump identification information from a transmitting unit associated with a medical pump at a receiving unit installed in a bed, wherein the medical pump is in physical proximity to the bed, and wherein the pump identification information is received only when the transmitting unit of the medical pump is within physical proximity of the receiving unit, wherein the medical pump comprises a start operation unit to allow the medical pump to start a pumping operation;
   associating the bed, which has received the pump identification information, with the medical pump that provided the pump identification information;
   displaying an operating state of the medical pump associated with the bed in accordance with an instruction received by an input/output control unit in association with the bed; and
   the input/output control unit allowing the pump to be operated by the start operation unit if the input/output control unit recognizes that the medical pump is a pump associated with the bed within a prejudged interval.

18. The non-transitory computer readable medium according to claim 17, wherein the bed is arranged in a management region, and wherein the method further comprises:
   receiving second pump identification information, from an entrance receiving unit, when the second medical pump enters the management region; and
   causing the second medical pump, not associated with the bed but which the pump identification information has been received by the entrance receiving unit, to be displayed as a non-associated pump.

19. The non-transitory computer readable medium according to claim 18, further comprising:
   canceling an associated state, of the medical pump, with respect to the bed only when the medical pump is judged to be in a stopped state of operating; and
   causing the medical pump, having the cancelled associated state and still within the management region, to be displayed as a second non-associated pump.

20. The non-transitory computer readable medium according to claim 18, further comprising:
   allowing the medical pump to start a pumping operation only if the medical pump remains associated with the bed; and
   starting a pumping operation on the medical pump, if the pumping operation is allowed.

* * * * *